United States Patent [19]

Sharrow

[11] Patent Number: 4,793,359
[45] Date of Patent: Dec. 27, 1988

[54] CENTERING BALLOON STRUCTURE FOR TRANSLUMINAL ANGIOPLASTY CATHETER

[75] Inventor: James S. Sharrow, Bloomington, Minn.

[73] Assignee: GV Medical, Inc., Minneapolis, Minn.

[21] Appl. No.: 41,996

[22] Filed: Apr. 24, 1987

[51] Int. Cl.[4] ............................................. A61B 10/00
[52] U.S. Cl. ................................ 128/658; 128/303.1; 128/344; 604/96
[58] Field of Search ......................... 128/653, 656–658, 128/772, 303.1, 341, 344, 395–398; 604/96–104

[56] References Cited

U.S. PATENT DOCUMENTS

| | | |
|---|---|---|
| 3,675,658 | 7/1972 | Taylor . |
| 3,866,599 | 2/1975 | Johnson ........................... 604/96 X |
| 4,033,331 | 7/1977 | Guss et al. . |
| 4,150,676 | 4/1979 | Jackson . |
| 4,213,461 | 7/1980 | Pevsner ............................ 128/656 X |
| 4,299,226 | 11/1981 | Banka . |
| 4,543,090 | 9/1985 | McCoy . |
| 4,545,390 | 10/1985 | Leery ................................ 128/772 |
| 4,571,240 | 2/1986 | Samson et al. .................. 128/658 X |
| 4,616,653 | 10/1986 | Samson et al. .................. 128/657 X |
| 4,665,925 | 5/1987 | Millar ............................... 604/96 X |
| 4,669,465 | 6/1987 | Moore et al. .................... 128/303.1 |
| 4,684,363 | 8/1987 | Ari et al. .......................... 128/344 X |

Primary Examiner—Kyle L. Howells
Assistant Examiner—Angela D. Sykes
Attorney, Agent, or Firm—Orrin M. Haugen; Thomas J. Nikolai; Frederick W. Niebuhr

[57] ABSTRACT

Disclosed is a cylindrical balloon mounted near the distal tip of a percutaneous transluminal laser angioplasty catheter. Proximal and distal neck sections of the balloon are sealed to the catheter tubing, and a balloon inflation lumen originating at the tubing proximal end is open to the balloon interior. An elongate cylindrical body of the balloon is joined to the distal neck by a substantially transverse distal wall. As the balloon dilates in response to fluid under pressure supplied to the lumen, the distal wall tends to position the distal neck and distal end of the catheter tubing in centered, coaxial relation to the balloon body.

10 Claims, 1 Drawing Sheet

CENTERING BALLOON STRUCTURE FOR TRANSLUMINAL ANGIOPLASTY CATHETER

BACKGROUND OF THE INVENTION

This invention relates to angioplasty catheters, and more particularly to percutaneous transluminal laser angioplasty catheters.

The treatment of occlusions, in arteries and blood vessels in general, using an angioplasty catheter equipped with an inflatable balloon at its distal tip, is well known. A more recent technique involves providing an optical fiber in such a catheter, and extending the distal end of the fiber slightly beyond the distal tip of the catheter, whereby laser energy generated at the proximal end of the fiber is transmitted to an occlusion to be treated. For a further explanation of this technique, reference is made to U.S. Pat. No. 4,669,465 and U.S. patent application Ser. No. 887,196 filed July 12, 1986, both assigned to the assignee of this application. An important requirement in using this technique is the proper positioning and orientation of the catheter distal tip. Precise positioning is essential to ensure that laser energy from the optical fiber is directed away from the arterial wall. Improper aiming can result in wall damage or even rupture to the artery.

Apparatus for positioning a catheter distal tip is known, although not necessarily in connection with transmission of laser energy in the catheter. For example, U.S. Pat. No. 4,545,390 to Leary granted Oct. 8, 1985 shows a guide wire with a helical spring attached to a tapered distal end. An extension of the spring is flexible and can be bent into a curve, whereupon insertion can be guided by rotation of the guide wire at the proximal end. U.S. Pat. No. 4,033,331 to Guss et al granted July 5, 1977 shows a catheter having a bend at its distal end, and a contour wire which can be inserted varying amounts to gradually straighten the bend. Somewhat related subject matter is disclosed in U.S. Pat. No. 4,150,676 to Jackson granted April 24, 1979. An endotracheal tube disclosed by Jackson has an inflatable balloon cuff at its distal end. A filament in a lumen runs the length of the tube, and can be pulled to increase the curvature at the distal end. While each of the devices disclosed in these patents is perhaps suitable for its particular environment, the patents fail to adequately address the need for the precise catheter tip positioning required in laser enhanced angioplasty catheters.

Therefore, it is an object of the present invention to provide a means for accurately establishing the position and orientation of the distal tip of a laser angioplasty catheter when it is inserted int an artery or other vessel.

Another object of the invention is to provide a balloon near the tip of an angioplasty catheter, which balloon is particularly well adapted for centering the catheter distal tip within an artery.

Yet another object of the invention is to provide a catheter balloon adapted for orienting the distal tip of the catheter in response to balloon dilation.

SUMMARY OF THE INVENTION

To achieve these and other objects, there is provided a catheter balloon for attachment in surrounding relation to an angioplasty catheter. The balloon includes an elongate tubular member formed of a pliable material, including coaxial proximal and distal end mounting segments for substantially fluid-tight attachment of said tubular member to a length of pliable catheter tubing extended through the tubular member. The balloon includes an elongate medial segment between and coaxial with the end mounting segments. The medial segment has a substantially larger diameter than the diameter of the end mounting segments, and is collapsible to an effective diameter slightly larger than the end mounting segment diameters. The tubular member further includes a substantially transverse distal end wall connected to the medial segment and to the distal end mounting segment.

Another aspect of the present invention is a laser enhanced translumsinal angioplasty catheter. The catheter includes a length of pliable catheter tubing insertable by its distal end into an artery, and a first lumen in the catheter tubing extends from its proximal end to the distal end. An optical fiber is provided in the first lumen for transmitting laser energy from the proximal end of the catheter tubing to the distal end. A catheter balloon is mounted to the catheter tubing in surrounding relation thereto and positioned proximate the distal end of the catheter tubing such that a distal tip of the catheter tubing extends distally beyond the balloon. A second lumen in the catheter tubing extends from the proximal end of the catheter tubing to a point near the distal end and open to the interior of the balloon. The balloon, in response to a fluid supplied under pressure through the second lumen, dilates to a generally cylindrical configuration to engage a segment of the artery to substantially axially align the balloon and the arterial segment about a central axis. The balloon includes a distal wall portion substantially perpendicular to the central axis and joined to the distal tip.

Preferably the length of the distal tip is substantially less than the diameter of the balloon. Further, radiopaque markers can be provided along the distal section and on the distal tip.

The perpendicular or transverse distal wall, in contrast to the gradually tapered distal walls in conventional catheter balloons, positively and consistently places the catheter tip in centered, coaxial relation to the balloon when the balloon is inflated. At the same time, balloon inflation positions the balloon in coaxial relation to its contiguous arterial segment. The result is a distal tip coaxial and centered in relation to the arterial segment. With the severe profile of the distal walls and a shortened distal tip, the catheter tip and balloon may be moved in near proximity to an occlusion requiring treatment, to further ensure that the laser energy from the catheter will be directed upon the occlusion. Thus, a percutaneous transluminal laser angioplasty catheter constructed in accordance with the present invention is well suited for accurate centering of the catheter tip, and is particularly useful in substantially straight arterial segments.

IN THE DRAWINGS

For a better appreciation of the above and other features and advantages, reference is made to the following detailed description and drawings, in which.

DETAILED DESCRIPTION OF THE PREFERRED EMBODIMENT

Figure 1:
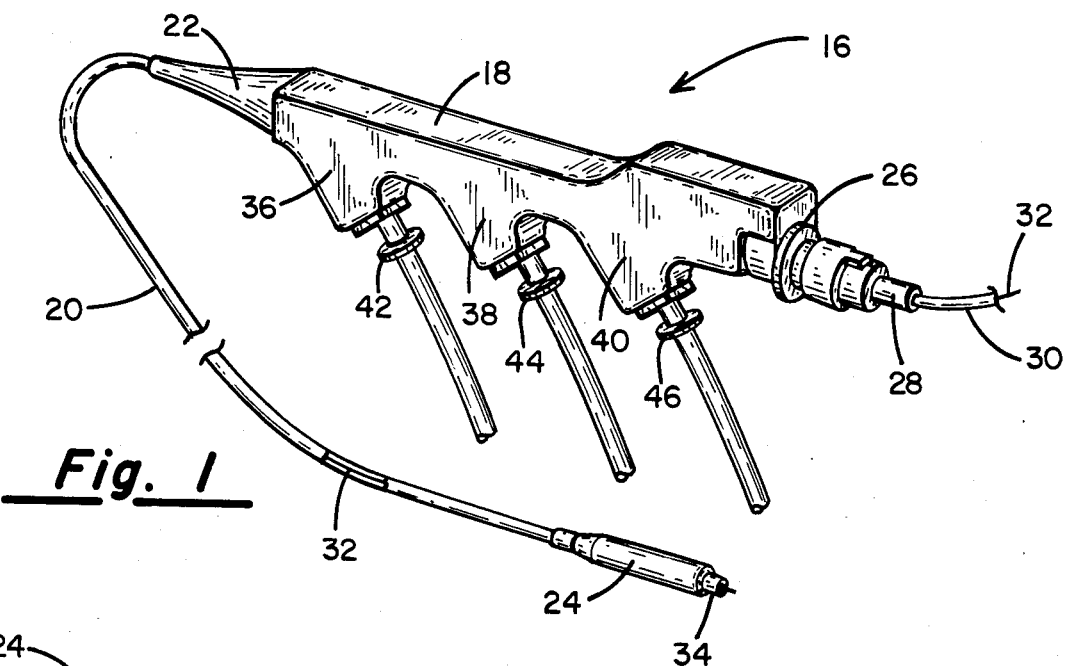
FIG. 1 is a perspective view of a laser enhanced transluminal angioplasty catheter equipped with a catheter balloon constructed in accordance with the present invention.

Turning now to the drawings, there is shown in FIG. 1 a transluminal angioplasty balloon catheter 16 including a catheter manifold 18 and a length of pliable catheter tubing 20 attached to the catheter manifold and reinforced by a conical strain relief member 22. An elongate catheter balloon 24 surrounds a distal region of catheter tubing 20 near the distal end of the tubing.

Joined to the proximal end of manifold 18, through a manifold connector 26 and a sheath connector 28, is an optical fiber sheath 30 containing an optical fiber 32. Sheath 30 is connected at its proximal end to a fiber advance housing which is not illustrated. For more information concerning such a housing and its relation to the catheter manifold, reference is made to U.S. Pat. No. 4,669,465 and U.S. patent application Ser. No. 915,507, now abandoned, filed Oct. 6, 1986, and assigned to the assignee of this application. Briefly, the fiber advance housing and fiber 32 are moved distally relative to catheter manifold 18 and sheath 30 to advance optical fiber 32 into catheter tubing 20, eventually to a point near a distal tip 34 of the tubing.

Catheter manifold 18 includes first, second and third extensions 36, 38 and 40, to which are connected first, second and third luer fittings 42, 44 and 46. First luer fitting 42 provides fluids to a balloon inflation lumen 48 (FIG. 5) running through catheter tubing 20 and open to the interior of balloon 24, thus to control dilation and deflation of the balloon. Second and third luer fittings 44 and 46 deliver treatment fluids, as needed, to a central lumen 50 also running through the catheter tubing and open to the distal end of the tubing.

Figure 2:
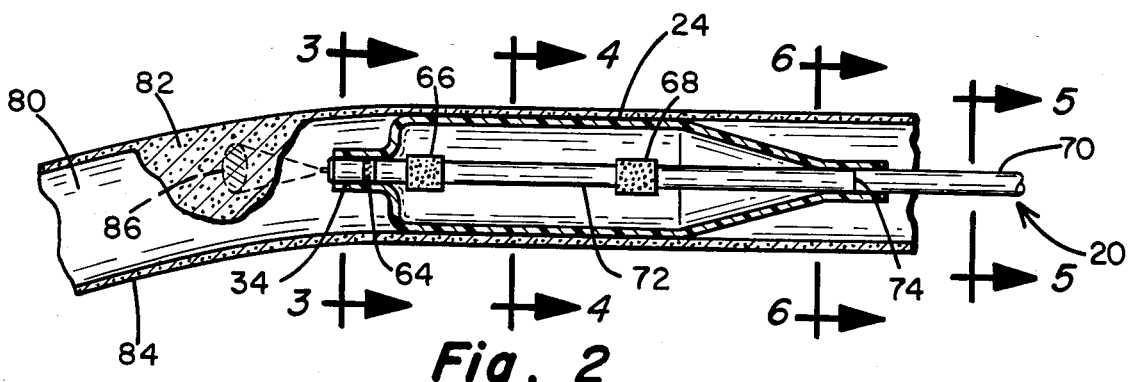
FIG. 2 is an enlarged side elevation of the balloon shown in FIG. 1 positioned within an artery, with portions of the artery and balloon wall removed for enhanced illustration of particular features.
Figures 6, 7:
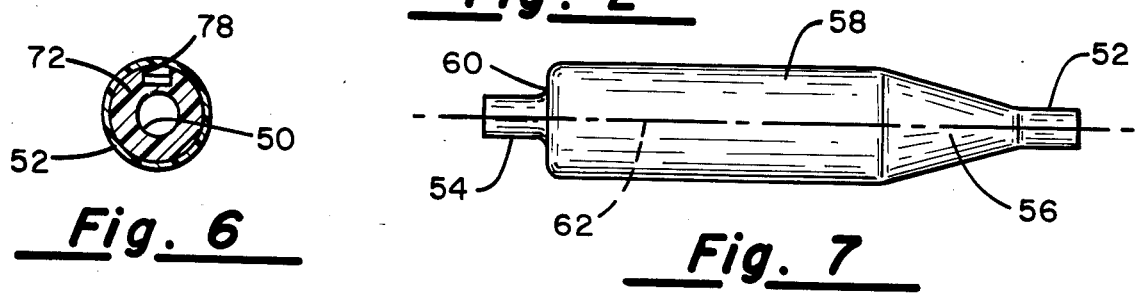
FIG. 6 is a sectional view taken along the line 6—6 in FIG. 2.
FIG. 7 is a side elevation of the balloon.

With reference to FIGS. 2 and 7, balloon 24 is essentially a tubular member constructed of a material such as polyolefin, or other material suitable for maintaining integrity of the balloon configuration when under fluid pressure during normal usage. The balloon has end mounting sections including a proximal neck 52 and a distal neck 54, each of which is sealed to catheter tubing 20. A proximal section of the balloon is gradually tapered, diverging forwardly from proximal neck 52 to an elongate medial section 58 which is cylindrical when balloon 24 is inflated. Joining distal neck 54 and medial section 58 is an annular, transverse distal wall 60, which is substantially perpendicular to a central longitudinal axis 62 of the balloon. Wall 60 provides a severe profile or blunt distal end in the balloon, the purpose of which is later explained. The balloon is symmetrical about axis 62.

A tip marker 64 is formed of an endless band of radiopaque (radio opaque) material such as platinum or gold, and is mounted around the catheter tubing at distal tip 34. When catheter tubing 20 is inserted into an artery, tip marker 64 provides a visual indication of the position of the distal tip. Somewhat larger radiopaque endless bands, particularly a distal balloon marker 66 and a proximal balloon marker 68, are wrapped around the distal region of the catheter tubing 72 contained within balloon 24. Balloon markers 66 and 68 are used to indicate the dilitating length of balloon 24 when in an artery. Markers 64, 66 and 68 together can confirm a centered, coaxial relation between distal tip 34 and balloon 24.

Preferably, catheter tubing 20 includes a main tubing section 70 and a distal tubing section 72, joined to one another at a butt seal 74 surrounded by proximal neck 52. The distal section includes the distal region plus the part of the tubing at distal tip 34. Distal section 72 is annular in cross-section (FIGS. 3 and 4), and preferably is formed of polyethylene and by extrusion. The tip marker and balloon markers have a similar configuration.

Figures 3, 4, 5:
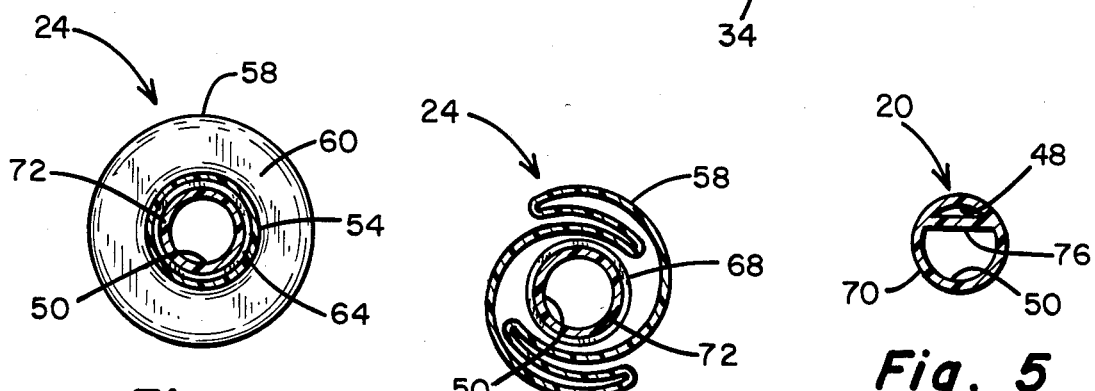
FIG. 3 is a sectional view taken along the line 3—3 in FIG. 2 and showing just the balloon.
FIG. 4 is a sectional view taken along the line 4—4 in FIG. 2, showing just the balloon, deflated.
FIG. 5 is a sectional view taken along the line 5—5 in FIG. 2.

FIG. 3 shows tip marker 64 surrounding distal section 72 of the tubing and in turn surrounded by distal neck 54, as well as the substantially cylindrical configuration of medial section 58 when balloon 24 is inflated. By contrast, FIG. 4 illustrates that the balloon when deflated can be confined to an effective diameter slightly larger than the neck diameters. Further it is seen that the distal section 72, over the majority of its length, includes just central lumen 50.

From FIG. 5 it is apparent that main section 70 of the catheter tubing includes balloon inflation lumen 48 and central lumen 50. A boundary 76 runs the length of the main section to separate the central and balloon inflation lumens.

As shown in FIG. 6, a cut-out 78 is formed in the proximal portion of distal section 72 of the catheter tubing, beginning at butt seal 74. Cut-out 78 forms a continuation of balloon inflation lumen 48, whereby the balloon inflation lumen is open to the interior of balloon 24.

Use of catheter 16, and the advantage afforded by the structure of balloon 24, are best appreciated from FIG. 2, showing catheter tubing 20 and balloon 24 contained within a generally cylindrical artery 80. A partial occlusion or blockage 82 has formed in a slightly curved portion of artery 80, and the catheter tubing is inserted into the artery to remove the occlusion 82 according to a procedure now described.

Initially, all air is removed from balloon 24 and inflation lumen 48, so that the balloon tends to assume the collapsed configuration shown in FIG. 4. Another preliminary step is to introduce a "contrast medium" into artery 80 to map the artery, thus to accurately locate occlusion 82 and to determine the required length and diameter of catheter balloon 24.

Following these steps, the catheter tubing is introduced percutaneously into artery 80, and moved along the artery until the distal region of the tubing is in a predetermined treatment position corresponding to the location shown in FIG. 2. The introduction and positioning is accomplished by using a guide wire as explained in U.S. patent application Ser. No. 916,238, filed Oct. 7, 1986 and assigned to the assignee of this application. Following positioning, the guide wire is withdrawn and optical fiber 32 is inserted into and through central lumen 50 until its distal end is at least proximate the distal end of tubing 20. Meanwhile, suction is applied to balloon inflation lumen 48 in order to maintain the balloon in its reduced shape.

Following optical fiber insertion, fluid under pressure is introduced to balloon 24 to inflate it to a selected pressure, for example two atmospheres. This causes the balloon to dilate and engage an arterial wall 84, thus to align balloon 24 coaxially with the segment of artery 80 contiguous with the balloon. Inflation of the balloon further positions distal tip 34 in coaxial relation to the balloon, and thus substantially coaxial and centered with respect to artery 80.

A feature of the present invention resides in the provision of distal wall 60, substantially transverse relative to the elongated balloon and distal tip 34. This orientation provides a blunt surface which rapidly and reliably positions the distal tip in its coaxial relation to the balloon each time the balloon is inflated. Conventional balloons have been provided with a gradually tapered tip, resembling proximal section 56, primarily to aid catheter insertion. As compared to such a gradual tip, the blunt tip more accurately positions the distal tip in the required coaxial relation. In fact, tests have shown that the blunt tip balloon consistently exhibits good tip centering, as compared to the tendency of tapered tips to lie against arterial walls.

Following balloon inflation, the next step is to advance optical fiber 32 so that its distal end extends slightly beyond distal tip 34. Then, laser energy is applied to the proximal end of the optical fiber, and transmitted beyond the optical fiber distal end to treat occlusion 82.

While ideally suited for use in straight arterial segments, catheter 16 can be used in slightly curved segments such as shown in FIG. 2, for example with a radius of curvature no smaller than thirteen inches. The use in curved arterial segments is facilitated not only by the accurate positioning afforded by transverse distal wall 60, but also due to the length of distal tip 34, which is selected to be less than the diameter of distal wall 60 when balloon 24 is inflated. This permits the balloon, as well as the end of distal tip 34, to be positioned near the occlusion, enchancing the utility of balloon marker 64 for determining distal tip positioning. With the balloon positioned as indicated in FIG. 2, a laser source at the proximal end of optical fiber 32 is activated and a "hot spot" 86 of laser energy is directed onto the occlusion for treatment.

Thus, the blunt forward wall of the balloon aligns the distal tip coaxially with the balloon and in spaced relation from the arterial wall in response to fluid pressure in the balloon. The tip and balloon markers indicate the position of the distal tip and balloon, which can be used in connection with arterial mapping to confirm the proper position of the balloon and distal tip before firing of the laser.

What is claimed is:

1. A laser enhanced transluminal angioplasty catheter, including:
    a length of pliable catheter tubing having proximal and distal ends and being insertable by its distal end into an artery, and means forming a first lumen in said catheter tubing extending from its proximal end to the distal end;
    an optical fiber in said first lumen for transmitting laser energy from the proximal end of the catheter tubing to the distal end;
    a catheter balloon mounted to said catheter tubing in surrounding relation thereto at a distal region of the catheter tubing such that a distal tip of the catheter tubing extends slightly beyond said balloon;
    means forming a second lumen in said catheter tubing, extending from the proximal end of the catheter tubing to a point near said distal end and open to the interior of said balloon; said balloon, in response to a fluid supplied under pressure through said second lumen, dilating to a generally cylindrical configuration to engage a segment of said artery to substantially axially align said balloon and said arterial segment about a central axis; and
    wherein said balloon, when is said cylindrical configuration, includes a distal wall substantially perpendicular to said central axis and joined with respect to said distal tip in surrounding relation thereto, said distal wall tending to position said distal tip parallel to said balloon and spaced apart from said arterial segment.

2. The catheter of claim 1 wherein:
    the length of said distal tip is substantially less then the diameter of said distal wall when said balloon is inflated.

3. The catheter of claim 1 the distal region having proximal and distal ends, including:
    a first radiopaque marker near the proximal end of said distal region, and a second radiopaque marker near the distal end of said distal region.

4. The catheter of claim 3 including:
    a third radiopaque marker on said distal tip.

5. The laser enhanced transluminal angioplasty catheter of claim 4 wherein:
    said catheter balloon is constructed of a pliable and substantially inextensible material.

6. An apparatus for controllably positioning the distal tip of a catheter with respect to a segment of an artery in which the catheter is inserted, including:
    a pliable length of catheter tubing having proximal and distal ends and being insertable by a distal end thereof into an artery;
    means forming an optical fiber lumen in said tubing from the proximal end to the distal end of said tubing, and an optical fiber contained in said lumen for transmitting laser energy to said distal end, said optical fiber being positionable distally beyond a distal tip of said tubing; and
    a catheter balloon attached to a distal region of said catheter tubing in surrounding relation to said tubing and adjacent said distal tip, said balloon adapted to undergo dilatation and assume a cylindrical configuration in response to a balloon inflation means, thereby to engage a segment of said artery and coaxially align said balloon and arterial segment about a central axis; said balloon when in said cylindrical configuration including a distal wall substantially normal to said central axis and connected to said distal tip, for positioning said distal tip coaxially on said central axis and in paced apart relation to said arterial segment.

7. The apparatus of claim 6 wherein:
    said balloon includes a proximal section gradually converging to said catheter tubing.

8. The apparatus of claim 6 wherein:
    said balloon inflation means includes a fluid supplied under pressure through a balloon inflation lumen in said tubing and open to the interior of said balloon.

9. The apparatus of claim 6 wherein:
    the length of said distal tip is substantially less than the diameter of said distal wall when the balloon is inflated.

10. The apparatus of claim 6 wherein:
    said catheter balloon is constructed of a pliable and substantially inextensible material.

* * * * *

UNITED STATES PATENT AND TRADEMARK OFFICE
CERTIFICATE OF CORRECTION

PATENT NO. : 4,793,359

DATED : December 27, 1988

INVENTOR(S) : James S. Sharrow

It is certified that error appears in the above-identified patent and that said Letters Patent is hereby corrected as shown below:

Column 6, Line 16, "then" should read -- than --.

Column 6, line 53, "paced" should read -- spaced --.

Signed and Sealed this

Twenty-third Day of May, 1989

Attest:

DONALD J. QUIGG

*Attesting Officer*   *Commissioner of Patents and Trademarks*